United States Patent [19]

Ong et al.

[11] Patent Number: 4,606,861

[45] Date of Patent: Aug. 19, 1986

[54] PROCESS FOR OBTAINING ANTHRAQUINODIMETHANE DERIVATIVES AND ANTHRONE DERIVATIVES

[75] Inventors: Beng S. Ong, Mississauga; Barkev Keoshkerian, Willowdale, both of Canada

[73] Assignee: Xerox Corporation, Stamford, Conn.

[21] Appl. No.: 709,866

[22] Filed: Mar. 8, 1985

[51] Int. Cl.$^4$ ............................................. C07C 50/16
[52] U.S. Cl. ................................ 260/351; 260/396 N; 430/58
[58] Field of Search ............................ 260/351, 396 N

[56] References Cited

U.S. PATENT DOCUMENTS 3,115,506 12/1963 Acker et al. ...................... 260/396

Primary Examiner—Dolph H. Torrence
Attorney, Agent, or Firm—E. O. Palazzo

[57] ABSTRACT

Disclosed is a process for the preparation of anthraquinodimethane derivatives and anthrone derivatives useful as electron transporting molecules which comprises the condensation reaction of anthraquinones with active methylene compounds in the presence of a Lewis acid and a base.

33 Claims, 3 Drawing Figures

PROCESS FOR OBTAINING ANTHRAQUINODIMETHANE DERIVATIVES AND ANTHRONE DERIVATIVES

BACKGROUND OF THE INVENTION

This invention is generally directed to processes for the preparation of electron transporting compounds, and more specifically the present invention is directed to specific processes for obtaining anthraquinodimethane derivatives and related anthrone derivatives. Therefore, in one embodiment of the present invention there are prepared anthraquinone and anthrone derivatives by the reaction of an anthraquinodimethane with active methylene compounds, inclusive of malononitrile, in a suitable organic solvent, which reaction is accomplished in the presence of a base and a Lewis acid. The resulting anthraquinodimethane derivatives and related anthrone derivatives are useful as electron transporting compounds in imaging members containing therein a photogenerating layer. These imaging members are the claimed subject matter of a copending application U.S. Ser. No. 709,867 entitled Photoresponsive Imaging Members With Electron Transporting Layers, the disclosure of this copending application being totally incorporated herein by reference.

The generation and development of electrostatic latent images on the surfaces of photoconductive materials by electrostatic means is well known. One electrostatic method involves the formation of a latent image on the surface of a photosensitive plate, or a photoreceptor. These photoreceptors can be comprised of a conductive substrate containing on its surface a layer of photoconductive insulating material, and in many instances there can be incorporated therein a thin barrier layer between the substrate and the photoconductive layer to prevent charge injection into the photoconductive layer upon charging of its surface, which injection would adversely affect the quality of the resulting image.

Numerous different xerographic photoconductive members are known including, for example, a homogeneous layer of a single material such as vitreous selenium, or composite layered devices, with a photoconductive substance dispersed in other substances. An example of one type of composite photoconductive layer used in xerography is described, for example, in U.S. Pat. No. 3,121,006 wherein there is disclosed a number of layers comprising finely divided particles of a photoconductive inorganic compound dispersed in an electrically insulating organic resin binder. In a commercial form, the binder layer contains particles of zinc oxide uniformly dispersed therein and coated on a paper backing. The binder materials disclosed in this patent comprise a material which is incapable of transporting for any significant distance injected charge carriers generated by the photoconductive particles. Accordingly, as a result the photoconductive particles must be in a substantially contiguous particle to particle contact throughout the layer for the purpose of permitting charge dissipation required for a cyclic operation. Illustrative examples of specific binder materials disclosed in this patent include, for example, polycarbonate resins, polyester resins, polyamide resins and the like.

There are also known photoreceptor materials comprised of other inorganic or organic materials wherein the charge carrier generation and charge carrier transport functions are accomplished by discrete contiguous layers. Additionally, photoreceptors are disclosed in the prior art which include an overcoating layer of an electrically insulating polymeric material and in conjunction with this overcoated type photoreceptor there have been proposed a number of imaging methods. However, the art of xerography continues to advance and more stringent demands need to be met by the copying apparatus for increased performance. Additionally, positively charged layered photoresponsive imaging members are needed for generating images of acceptable resolution, and substantially no undesirable background deposits.

Recently, there has been disclosed layered photoresponsive devices comprised of generating layers and hole transport layers, reference U.S. Pat. No. 4,265,990, and overcoated photoresponsive materials with a conductive layer, overcoated with a hole transport layer followed by an overcoating of a photogenerating layer and a top coating of an insulating organic resin, reference U.S. Pat. No. 4,251,612. Examples of generating layers disclosed in these patents include trigonal selenium and phthalocyanines, while examples of the active transport layer molecules that may be employed are comprised of certain diamines as mentioned herein. The disclosures of each of these patents, namely U.S. Pat. Nos. 4,265,990 and 4,251,612, are totally incorporated herein by reference.

Many other patents are in existence describing layered photoresponsive devices with generating pigments such as U.S. Pat. No. 3,041,167, which discloses an electrophotographic imaging process employing an overcoated imaging member containing a conductive substrate, a photoconductive insulating layer, and an overcoating layer of an electrically insulating polymeric material. This member is utilized in an electrophotographic copying method by, for example, initially charging the member with an electrostatic charge of a first polarity and imagewise exposing to form an electrostatic latent image which can be subsequently developed to form a visible image. Prior to each succeeding imaging cycle, the member can be charged with an electrostatic charge of a second polarity which is opposite in polarity to the first polarity. Sufficient additional charges of the second polarity are applied so as to create across the member a net electrical field of the second polarity. Simultaneously, mobile charges of the first polarity are created in the photoconductive layer such as by applying an electrical potential to the conductive substrate. The imaging potential which is developed to form the visible image is present across the photoconductive layer and the overcoating layer.

Other representative prior art disclosing layered photoresponsive devices include U.S. Pat. Nos. 4,115,116; 4,047,949; 4,081,274 and 4,315,981. According to the disclosure of the '981 patent, the recording member consists of an electroconductive support, a photoconductive layer of organic materials which contain a charge carrier producing dyestuff layer of a compound having an aromatic, or heterocyclic polynuclear quinone ring system, and a charge transport layer.

Furthermore, there is disclosed in U.S. Pat. No. 4,135,928 electrophotographic light sensitive members comprised of 7-nitro-2-aza-9-fluroenylidene-malononitrile as charge transporting substances. According to the disclosure of this patent, the electrophotograhic light sensitive members are comprised of an electroconductive support, a layer thereover of a photogenerating substance, and 7-nitro-2-aza-9-fluorenylidene-malononitrile of the formula, for example, as illustrated in column 1.

There is also disclosed in U.S. Pat. No. 4,474,865 imaging members with electron transporting layers of fluorenylidene derivatives. These electron transporting compounds differ from those of the present invention in that they are based on the fluorenone structure with a 5-member central ring; while the transporting compounds of the present invention are based on anthrone and anthraquinone structures which contain a 6-member central ring. In addition, while the fluorenylidene derivatives are relatively planar in structure, the anthrone and anthraquinone derivatives of the present invention are buckled and assume a butterfly-like conformation.

While the above-described photoresponsive imaging members are suitable for their intended purposes there continues to be a need for improved imaging members, particularly layered imaging members, which not only generate acceptable images but which can be repeatedly used in a number of imaging cycles without deterioration thereof from the machine environment or surrounding conditions. Additionally, there continues to be a need for improved layered photoconductive imaging members wherein the materials selected are substantially inert to users of these members. Also, there continues to be a need for positively charged imaging members with electron transporting compounds. Additionally, there continues to be a need for improved photoresponsive imaging members which can be prepared with a minimum number of processing steps, and wherein the layers are sufficiently adhered to one another to allow the continuous use of these members in imaging and printing processes.

Also, there is a need for electron transport compounds which are compatible with common matrix polymers, inclusive of polycarbonates, and polyesters enabling the dispersion of these compounds to be maintained for the useful life of the layered imaging members. Moreover, there continues to be a need for a simple synthetic process for the preparation of anthrone, and anthraquinodimethane electron transporting compounds.

SUMMARY OF THE INVENTION

It is, therefore, an object of the present invention to provide an improved photoresponsive member which overcomes the above-noted disadvantages.

It is yet another object of the present invention to provide a process for the preparation of electron transporting compounds.

A further specific object of the present invention is the provision of an improved photoresponsive imaging member containing a photogenerating layer, and in contact therewith an electron transporting layer of anthrone derivatives prepared by the processes illustrated herein.

Another specific object of the present invention is the provision of an improved photoresponsive imaging member containing a photogenerating layer, and in contact therewith an electron transporting layer of anthraquinodimethane derivatives prepared by the processes illustrated herein.

The primary object of the present invention and other related objects are accomplished by the provision of processes for the preparation of anthraquinodimethane derivatives and anthrone derivatives useful as electron transporting molecules which comprises the condensation reaction of anthraquinones with active methylene compounds in the presence of a Lewis acid and a base. The aforementioned electron transporting compounds prepared in accordance with the process of the present invention are useful for incorporation into the layered photoresponsive imaging members are disclosed in the referenced copending application entitled Photoresponsive Imaging Members With Electron Transporting Layers.

Specific electron transporting molecules that can be prepared in accordance with the present invention are selected from the group consisting of anthrone derivatives and anthraquinodimethane derivatives of the following formulas:

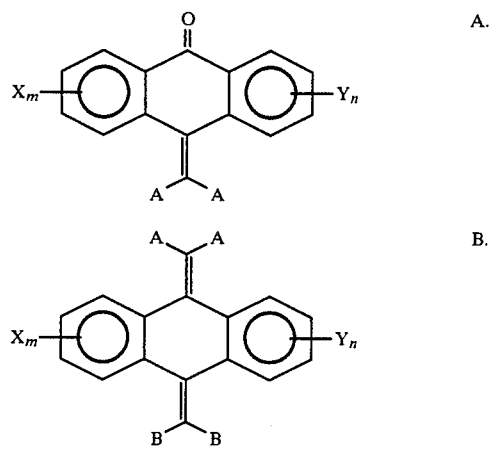

wherein A and B are independently selected from the group consisting of CN and COOR, wherein R is an alkyl group or an aryl group; X and Y are independently selected from the group consisting of alkyl, aryl, halide, hydroxy and electron withdrawing groups such as CN, $NO_2$, COR, COOR, and the like, wherein R is as defined herein, and m and n are numbers of from 0 to 3.

Illustrative examples of alkyl groups include those of from about 1 carbon atom to about 25 carbon atoms, and preferably of from one carbon atom, to about 8 carbon atoms, such as methyl, ethyl, propyl, butyl, pentyl, hexyl, octyl, nonyl, decyl, pentadecyl, stearyl, and the like, with methyl, ethyl, propyl, and butyl being preferred. Aryl substituents include those of from 6 carbon atoms to about 24 carbon atoms, such as phenyl and naphthyl. Halides include chloride, bromide, iodide and fluoride.

Specific examples of electron transporting compounds prepared in accordance with the process of the present invention include those represented by the following formulas:

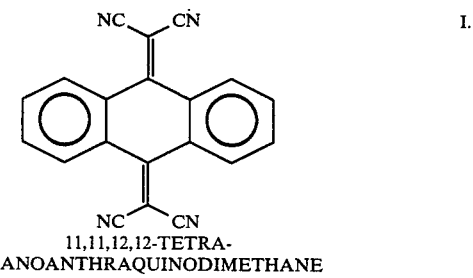

11,11,12,12-TETRA-
CYANOANTHRAQUINODIMETHANE

-continued

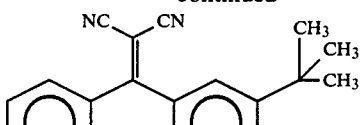

11,11,12,12,-TETRACYANO-2-TERT-BUTYLANTHRAQUINODIMETHANE

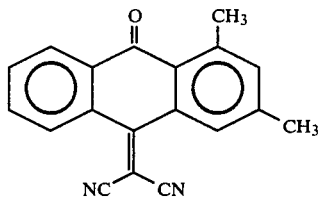

1,3-DIMETHYL-10-(DICYANOMETHYLENE)ANTHRONE

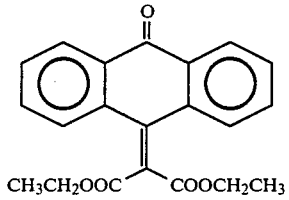

10-[BIS(ETHOXY-CARBONYL)METHYLENE]ANTHRONE

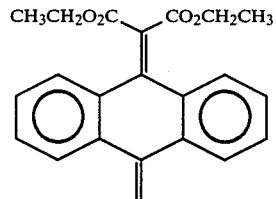

11,11,12,12-TETRAKIS(ETHOXY-CARBONYL)ANTHRAQUINODIMETHANE

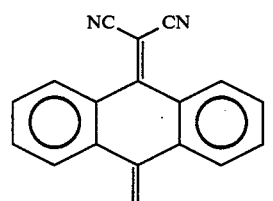

11,11-DICYANO-12,12-BIS(ETHOXY-CARBONYL)ANTHRAQUINODIMETHANE

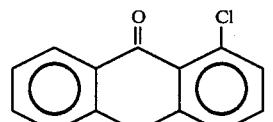

1-CHLORO-10-[BIS(ETHOXY-CARBONYL)METHYLENE]ANTHRONE

-continued

II.

III.

IV.

V.

VI.

VII.

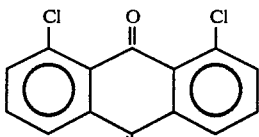

1,8-DICHLORO-10-[BIS(ETHOXY-CARBONYL)METHYLENE]ANTHRONE

VIII.

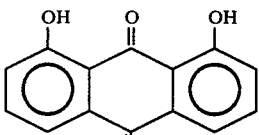

1,8-DIHYDROXY-10-[BIS(ETHOXY-CARBONYL)METHYLENE]ANTHRONE

IX.

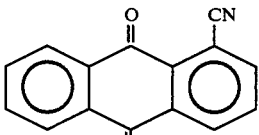

1-CYANO-10-[BIS(ETHOXY-CARBONYL)METHYLENE]ANTHRONE

X.

With further reference to the process of the present invention, the condensation reaction of the anthraquinone with active methylene compounds, inclusive of malononitrile, (dicyanomethane), malonate (bis[methoxycarbonyl]methane), dinitromethane, beta diketones, and the like, is affected in a suitable organic solvent at room temperature in the presence of a base and a Lewis acid. With the proper choice of reactants, both the 11,11,12,12-tetrasubstituted anthraquinodimethane and 10-disubstituted methylene anthrone derivatives can be obtained by similar synthetic process.

More specifically, the electron transporting anthrone derivatives are prepared by reacting 1 mole of an anthraquinone with 1 to 1.5 moles of an active methylene compound. The aforementioned condensation is affected in the presence of an excess, generally 2 to 5 moles, of a Lewis acid such as titanium tetrachloride and an excess, generally 4 to 20 moles, of a base inclusive of pyridine. Suitable solvents for the reaction include chlorinated compounds like methylene chloride, chloroform, and 1,2-dichloroethane; and ethyl acetate. Also, this reaction is usually initially accomplished at ice-bath temperatures, and then at room temperature.

Therefore, the preparation of anthrone derivatives, which can be purified by recrystallization or by chromatography, and are characterized by elemental analysis, spectroscopy and mass spectrometry, can be illustrated with reference to the following reaction scheme:

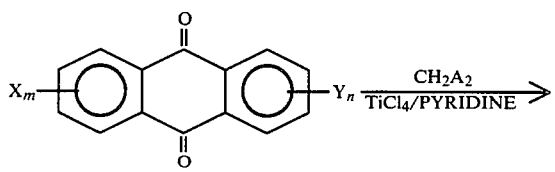

I.

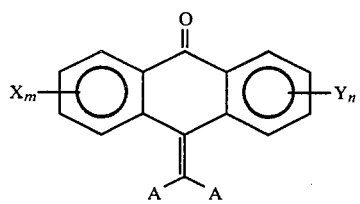

10

15 wherein X, Y, Z, m and n are as defined hereinbefore.

Similarly, the electron transporting anthraquinodimethane derivatives are synthesized by reacting 1 mole of an anthraquinone with 2 to 3 moles of an active methylene compounds such as malonoitrile, malonate, and the like. The aforementioned condensation is affected in the same manner with reference to the preparation of the anthrone derivatives except that additional Lewis acid and base are employed. Generally, thus for each mole of anthraquinone, 3 to 5 moles of titanium tetrachloride, and 6 to 25 moles of pyridine were used.

Accordingly, the preparation of anthraquinodimethane derivatives, which can be purified by simple recrystallization from a suitable solvent or by chromatography, and are characterized by elemental analysis, standard spectroscopic and mass spectrometric techniques, can be illustrated by the following reaction sequence:

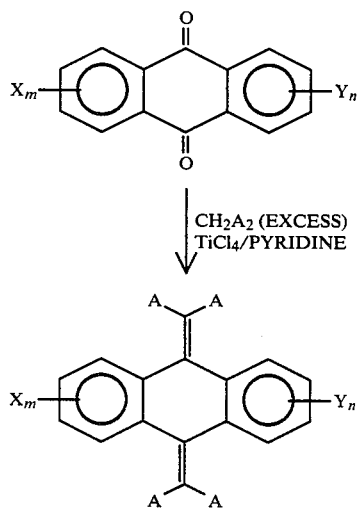

II.

wherein X, Y, A, m and n are as defined herein.

With further reference to the synthesis of the anthraquinodimethane derivatives with different substituents, that is, wherein the A substituent, for example, is CN, and the B substituents are COOR, at the carbon-11 and carbon-12 position, there is reacted 10-disubstituted methylene anthrones, with 1 to 1.5 moles of active methylene compounds, in accordance with the following reaction scheme (III). The aforementioned condensation is affected in the presence of an excess, generally 2 to 5 moles of a Lewis acid such as titanium tetrachloride, and an excess, generally 4 to 20 moles, of a base inclusive of pyridine. Suitable solvents for this reaction include chlorinated compounds like methylene chloride, chloroform, and 1,2-dichloroethane; and ethylacetate. Also, this reaction is usually initially accomplished at ice bath temperatures, and then at room temperature.

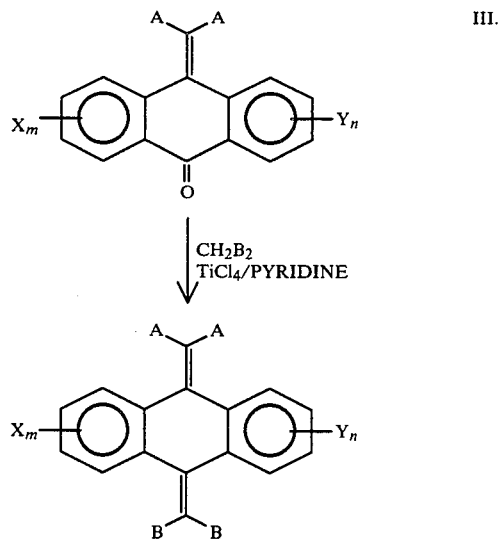

III.

wherein the A substituents are COOR, the B substituents are CN, and the other substituents are as defined herein.

With regard to all the reactions illustrated herein, the reaction temperature generally ranges from about 0° to about 30° C.

The electron transporting compounds prepared in accordance with the present invention are useful in layered photoresponsive imaging members as detailed, for example, in the drawings.

BRIEF DESCRIPTION OF THE DRAWINGS

For a better understanding of the present invention and further features thereof, reference is made to the following detailed description of various preferred embodiments wherein.

DESCRIPTION OF THE PREFERRED EMBODIMENTS

Figure 1:
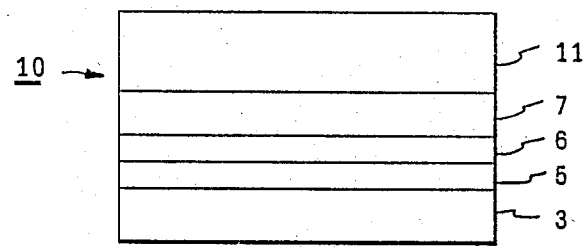
FIG. 1 is a partially schematic cross-sectional view of the improved photoresponsive imaging member of the present invention.

Illustrated in FIG. 1 is the improved photoresponsive imaging member of the present invention, generally designated 10; and comprising a substrate 3, an optional electron blocking layer 5, an adhesive layer 6, a charge carrier photogenerating layer 7, and an electron transporting layer 11, comprised of the anthraquinodimethane, and anthrone derivatives illustrated herein.

Figure 2:
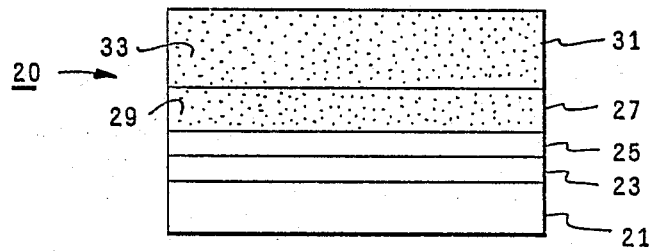
FIG. 2 is a partially schematic cross-sectional view of a preferred photoresponsive member of the present invention.

Illustrated in FIG. 2 is a preferred improved photoresponsive imaging member of the present invention, generally designated 20; and comprising a supporting substrate 21, an optional electron blocking layer 23, an adhesive layer 25, a charge carrier photogenerating layer 27 of trigonal selenium, or vanadyl phthalocyanine, optionally dispersed in an inactive resinous binder 29, and an electron transporting layer 31, comprised of the electron transporting anthrone compounds of the present invention dispersed in an inactive resinous binder 33.

Figure 3:
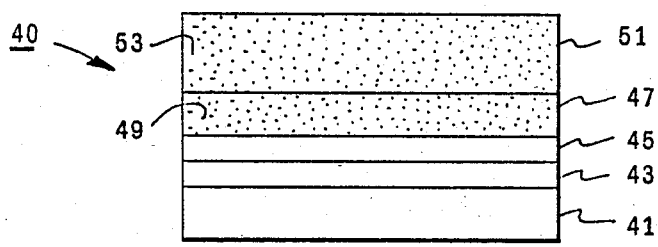
FIG. 3 illustrates another preferred photoresponsive imaging member of the present invention.

Illustrated in FIG. 3 is a preferred improved photoresponsive imaging member of the present invention, generally designated 40; and comprising a substrate 41, an optional electron blocking layer 43, an adhesive layer 45, a charge carrier photogenerating layer 47 of trigonal selenium, or vanadyl phthalocyanine, optionally dispersed in an inactive resinous binder 49, and an electron transporting layer 51, comprised of the electron transporting anthraquinodimethane compounds of the present invention dispersed in an inactive resinous binder 53.

The supporting substrate layers may be opaque or transparent and may comprise any suitable material having the requisite mechanical properties. Therefore, the substrate may comprise a layer of non-conducting material such as an inorganic or organic polymeric material with a conductive surface layer arranged thereon, or a conductive material inclusive of, for example, a metallized organic polymeric material, aluminum, chromium, nickel, indium, tin oxide, and brass. Also, the substrate may be flexible or rigid and may have many different configurations such as, for example, a plate, a cylindrical drum, a scroll, and an endless belt.

The thickness of the substrate layer depends on many factors, including economical considerations, thus this layer may be of substantial thickness, for example, over 100 mils or of minimum thickness providing the objectives of the present invention are accomplishedd. In one preferred embodiment, the thickness of the supporting substrate is from about 1 mil to about 50 mils.

As optional electron blocking layers there can be selected various suitable known materials including aluminum oxide, polysilanes and the like. The primary purpose of this layer is to provide electron blocking, that is, to prevent electron injection from the substrate during and after charging. Generally, this layer has a thickness of less than 50 Angstroms. The adhesive layer is typically a polymeric material, including polyesters such as DuPont 49,000 polyester, and the like. Generally, this layer has a thickness of about 0.1 micron.

Photogenerating layers can include therein known photoconductive charge carrier generating materials, such as amorphous selenium, selenium alloys, halogen doped amorphous selenium, halogen doped amorphous selenium alloys, trigonal selenium, selenite and carbonates with trigonal selenium, reference U.S. Pat. Nos. 4,232,102 and 4,233,283, the disclosures of which are totally incorporated herein by reference, copper and chlorine doped cadmium sulfide, cadmium selenide and cadmium sulfur selenide, and the like. Alloys of selenium included within the scope of the present invention are selenium tellurium alloys, selenium arsenic alloys, and preferably such alloys containing a halogen, such as chlorine in an amount of from about 50 to 200 parts per million. Other photogenerating layer pigments include metal phthalocyanines, metal free phthalocyanines, vanadyl phthalocyanines, other known phthalocyanines, reference U.S. Pat. No. 3,816,118, the disclosure of which is totally incorporated herein by reference, squarylium pigments, charge transfer complex materials, and various sensitizers such as cyanine dyes, and the like.

Typically, the photogenerating layer has a thickness of from about 0.05 microns to about 10 microns or more, and preferably is of a thickness of from about 0.4 microns to about 3 microns. Generally, however, the thickness of the photogenerating layer is dependent on the photogenerating pigment loading, which may vary from about 5 percent by volume to about 100 percent by volume; and other factors inclusive of mechanical considerations, for example; and whether a flexible photoresponsive imaging member is desired. Illustrative examples of polymeric binder resinous materials that can be selected for the photogenerating layer pigments include those as disclosed, for example, in U.S. Pat. No. 3,121,006, the disclosure of which is totally incorporated herein by reference, polyesters, polycarbonate resins, polyvinyl carbazole, epoxy resins, phenoxy resins, and the like.

The electron transporting compounds of the present invention can also be dispersed in a resinous binder in an amount of from about 10 precent by weight to about 75 percent by weight, and preferably in an amount of from about 35 percent by weight to about 50 percent by weight. Illustrative examples of organic resinous material useful as a transport binder include polycarbonates, acrylate polymers, vinyl polymers, cellulose polymers, polyesters, polysiloxanes, polyamides, polyurethanes and epoxies, as well as block, random or alternating copolymers thereof. Preferred electrically inactive binder materials are polycarbonate resins having a molecular weight of from about 20,000 to about 100,000 with a molecular weight in the range of from about 50,000 to about 100,000 being particularly preferred. Also, this layer can be of various suitable thicknesses, and generally is of a width of from about 5 microns to about 80 microns.

There can be added to the electron transporting layer in an amount of from 1 percent by weight to about 30 percent by weight electron donor molecules such as ethylcarbazole, triphenylamines, and arylamines of the formula:

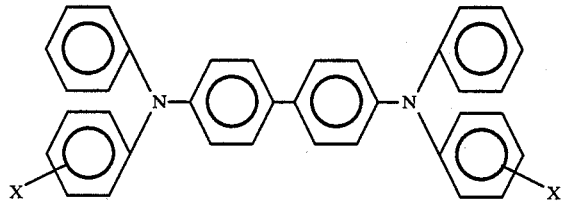

wherein X is selected from the group consisting of alkyl and halogen, especially (ortho) CH$_3$, (meta) CH$_3$, (para) CH$_3$, (ortho) Cl, (meta) Cl, and (para) Cl. These additives or dopants are selected to assist in ensuring the homogeneous dispersion of the transport molecules in the electron transport layer, which dispersion provides for improved transport properties.

Illustrative examples of aryl amine compounds encompassed by the aforementioned formula include, for example, N,N'-diphenyl-N,N'-bis(alkylphenyl)-[1,1'-diphenyl]-4,4'-diamine wherein alkyl is selected from the group consisting of methyl, ethyl, propyl, butyl, hexyl, and the like. With halogen substitution, the compound is N,N'-diphenyl-N,N'-bis(halo phenyl)-[1,1'-biphenyl]-4,4'-diamine.

The invention will now be described in detail with respect to specific preferred embodiments thereof, it being understood that these examples are intended to be illustrative only. Also, the invention is not intended to be limited to the materials, conditions, and process parameters recited therein. All parts and percentages are by weight unless otherwise indicated.

EXAMPLE I

Synthesis of 11,11,12,12-Tetracyanoanthraquinodimethane (I)

In a 500-milliliter (ml) round-bottomed flask equipped with a pressure equalizing dropping funnel, there was discharged 8.4 grams of anthraquinone, 7.0 grams of malononitrile and 200 milliliters of methylene chloride under a nitrogen atmosphere. The resulting mixture was stirred mechanically and cooled with an ice bath. Thereafter, 23 milliliters of titanium tetrachloride was added dropwise over a period of 20 minutes by means of the pressure equalizing funnel. Subsequently, there was added to the reaction mixture 65 milliliters of pyridine. The resulting reaction mixture was then stirred at room temperature for another 5 hours, and was then treated with a dilute aqueous hydrochloric acid solution while vigorously stirring. The solid product generated was filtered, washed several times with water and dried in a vacuo. Recrystallization from acetic acid afforded 6.0 grams of the above pure product, mp., greater than 350° C. (decomp.).

$^1$H NMR (CDCl$_3$), delta: 7.8–8.6 (AA'BB').

IR (KBr Pellet): 2235 cm$^{-1}$.

MS, m/e (relative intensity): 304 (100), 277 (30), 250 (20), 223 (8), 212 (5), 198 (6), 152 (7), 138 (9), 125 (19), 111 (14).

Elemental Analysis, calcd. for $C_{20}H_8N_4$: C, 78.94; H, 1.65; N, 18.41. Found: C, 78.94; H, 1.83; N, 18.29.

EXAMPLE II

Synthesis of 11,11,12,12-Tetracyano-2-tert-Butylanthraquinodimethane (II)

The synthesis of Compound (II) was accomplished on a 0.05 mole-scale in accordance with the procedure of Example I except that at the end of the reaction the mixture was worked up as follows:

The reaction mixture was then treated with a dilute aqueous hydrochloric acid solution, and the organic phase resulting was separated by means of a separatory funnel. Thereafter, the organic solution was washed three times with water, and dried with magnesium sulfate. Evaporation of the dried solution under reduced pressure afforded a solid residue which was purified by column chromatography on silica gel, yielding (59 percent), a pale yellow solid product, mp., 313°–314° C. The eluting solvent was a 1:4 mixture of ethyl acetate and hexane.

$^1$H NMR (CDCl$_3$), delta: 1.4 (s, 9H); 7.6–8.4 (m, 7H).

IR (KBr Pellet): 2235 cm$^{-1}$.

Elemental analysis, calcd. for $C_{24}H_{16}N_4$: C, 79.98; H, 4.47; N, 15.54. Found: C, 80.09; H, 4.40; N, 15.51.

EXAMPLE III

Synthesis of 1,3-Dimethyl-10-(Dicyanomethylene)Anthrone (III)

The preparation of Compound (III) was carried out on a 0.02 mole scale in accordance with the procedure of Example II. However, only a stoichiometric quantity of malononitrile was required; and 9.0 milliliters of titanium tetrachloride and 17 milliliters of pyridine were selected. The crude product was purified by crystallization from acetic acid yielding 4.5 grams of pure Compound (III), mp., 215°–216° C.

$^1$H NMR (CDCl$_3$), delta: 2.45 (s, 3H); 2.75 (s, 3H), 7.3–8.3 (m, 7H).

IR (KBr Pellet): 1680, 2230 cm$^{-1}$.

Elemental analysis, calcd. for $C_{19}H_{12}N_2O$: C, 80.26; H, 4.25; N, 9.85; O, 5.63. Found: C, 80.35; H, 4.23; N, 9.81; O, 5.67.

EXAMPLE IV

Synthesis of 10-[Bis(Ethoxycarbonyl)Methylene]Anthrone (IV) and 11,11,12,12-Tetrakis(Ethoxycarbonyl)Anthraquinodimethane (V)

In a 300 milliliter round bottomed flask equipped with a pressure equalizing dropping funnel there was added 10 grams of anthraquinone, 2.9 milliliters of diethyl malonate, and 150 milliliters of methylene chloride under a nitrogen atmosphere. The resulting mixture was then mechanically stirred and cooled with an ice bath. Thereafter, 43 milliliters of titanium tetrachloride was added dropwise by means of the dropping funnel over a period of 20 minutes, followed by the addition of 100 milliliters of pyridine. After addition, the reaction mixture was allowed to react at room temperature for 5 days. Subsequently, 300 milliliters of water was added to the reaction mixture with vigorous stirring, and the organic layer was separated. This layer was then washed twice with a dilute aqueous hydrochloric acid solution, and dried with anhydrous magnesium sulfate. Evaporation of the resulting organic solution yielded an oily residue. Column chromatographic separation on silica gel (ethyl acetae/hexane=1/9) afforded 8.4 grams of the monosubstituted product (IV), mp., 100°–102° C., and 3.5 grams of disubstituted product (V), mp., 137°–138° C.

10-Bis(ethoxycarbonyl)methylene anthrone (IV)

$^1$H NMR (CDCl$_3$), delta: 1.15 (t, 6H); 4.2 (q, 4H), 7.4–8.3 (m, 8H).

IR (KBr Pellet): 1680, 1745 cm$^{-1}$.

Elemental analysis, calcd. for $C_{21}H_{18}O_5$: C, 71.99; H, 5.18; O, 22.83. Found: C, 68.01; H, 5.72; O, 25.84.

11,11,12,12-Tetrakis(ethoxycarbonyl)anthraquinodimethane (V)

$^1$H NMR (CDCl$_3$), delta: 1.15 (t, 12H); 4.2 (m, 8H), 7.2–7.8 (m, 8H).

IR (KBr Pellet): 1745 cm$^{-1}$.

Elemental analysis, calcd. for $C_{28}H_{28}O_8$: C, 68.28; H, 5.73; O, 25.98. Found: C, 68.01; H, 5.72; O, 25.84.

EXAMPLE V

Synthesis of 11,11-Dicyano-12,12-Bis(Ethoxycarbonyl)Anthraquinodimethane (VI)

The preparation of Compound (VI) was accomplished in accordance with the procedure of Example III with 3.0 grams of 10-bis(ethoxycarbonyl)methylene anthrone (IV) as the starting material, in place of anthraquinone. The crude product was recrystallized from methanol yielding 2.1 grams of the pure Compound (VI), mp., 155°–156° C.

$^1$H NMR (CDCl$_3$), delta: 1.2 (t, 6H); 4.25 (q, 4H); 7.3–7.8 (m, 8H).

IR (KBr Pellet): 1750, 2240 cm$^{-1}$.

Elemental analysis, calcd. for C$_{24}$H$_{18}$N$_2$O$_4$: C, 72.35; H, 4.55; N, 7.03; O, 16.06. Found: C, 72.18; H, 4.66; N, 6.97; O, 16.03.

EXAMPLE VI

Synthesis of 1,8-Dichloro-10-[Bis(Ethoxycarbonyl)Methylene]-Anthrone (VIII)

In a 250 milliliter round-bottomed flask equipped with a pressure equalizing dropping funnel, there was discharged 10 grams of 1,8-dichloroanthraquinone, 16.5 milliliters of diethyl malonate, and 150 milliliters of methylene chloride under a nitrogen atmosphere. The resulting mixture was then mechanically stirred and cooled with an ice bath. Thereafter, 24 milliliters of titanium tetrachloride was added dropwise through the dropping funnel over a period of 20 minutes, followed by the addition of 45 milliliters of pyridine. The reaction mixture was then stirred at room temperature for 65 hours. Subsequently, 150 milliliters of a dilute aqueous hydrochloric acid solution was slowly added with stirring. The organic phase resulting was separated, washed twice with water, and dried with anhydrous magnesium sulfate. Evaporation of the dried organic solution yielded a yellowish solid which when recrystallized from methanol afforded 7.5 grams of the pure Compound (VIII), mp., 166°–167° C.

$^1$H NMR (CDCl$_3$), delta: 1.2 (t, 6H); 4.25 (q, 4H); 7.25–7.8 (m, 6H).

IR (KBr Pellet): 1700, 1745 cm$^{-1}$.

Elemental analysis, calcd. for C$_{21}$H$_{16}$Cl$_2$O$_5$: C, 60.16; H, 3.85; Cl, 16.91; O, 19.08. Found: C, 60.29; H, 3.75; Cl, 16.89; O, 19.05.

EXAMPLE VII

Synthesis of 1,8-Dihydroxy-10-[Bis(Ethoxycarbonyl)Methylene-]Anthrone (IX)

The synthesis of Compound (IX) was accomplished in accordance with the procedure of Example VI except that 1,8-dihydroxyanthraquinone was selected as the starting material in place of the 1,8-dichloroanthraquinone. The yield of the pure product (IX) was 24 percent; with a melting point of 147.5°–149° C.

$^1$H NMR (CDCl$_3$), delta: 1.15 (t, 6H); 4.2 (q, 4H); 7.0–7.5 (m, 6H); 11.85 (s, 2H).

IR (KBr Pellet): 1640, 1730, 3100 cm$^{-1}$.

Elemental analysis, calcd. for C$_{21}$H$_{18}$O$_7$: C, 65.96; H, 4.74; O, 29.29. Found: C, 66.18; H, 4.86; O, 29.10.

EXAMPLE VIII

A layered photoresponsive imaging member with Compound (IX) as synthesized in Example VII in a polycarbonate resinous binder as the electron transport layer, and trigonal selenium as the photogenerator, was prepared as follows:

A dispersion of trigonal selenium and poly(N-vinylcarbazole) was prepared by ball milling 1.6 grams of trigonal selenium and 1.6 grams of poly(N-vinylcarbazole) in 14 milliliters each of tetrahydrofuran and toluene. Ten grams of the resulting slurry was then diluted with a solution of 0.24 grams of N,N'-diphenyl-N,N'bis(3-methylphenyl)-[1,1'-biphenyl]-4,4'-diamine in 5 milliliters each of tetrahydrofuran and toluene. A 1.5 micron thick photogenerator layer was fabricated by coating the above dispersion onto an aluminized Mylar substrate, thickness of 2 mils, with a Bird Film applicator, followed by drying in a forced air oven at 135° C. for 5 minutes. A solution for the electron transport layer was then prepared by dissolving 1.0 grams of electron transport Compound (IX), 0.33 grams of N,N'-diphenyl-N,N'-bis(3-methylphenyl)-1,1'-biphenyl-4,4'-diamine, and 1.0 gram of Makrolon polycarbonate in 14 milliliters of methylene chloride. This solution was then coated over the photogenerator layer by means of a Bird Film applicator. The resulting member was then dried in a forced air oven at 130° C. for 30 minutes, resulting in an 18 micron thick transport layer.

The fabricated imaging member was then electrically tested by positively charging it with a corona, and discharged by exposing to white light of wavelengths of from 400–700 nanometers. Charging was accomplished with a single wire corotron in which the wire was contained in a grounded aluminum channel and was strung between two insulating blocks. The acceptance potential of this imaging member after charging, and its residual potential after exposure were recorded. The procedure was repeated for different exposure energies, supplied by a 75 watt Xenon arc lamp of incident radiation, and the exposure energy required to discharge the surface potential of the member to half of its original value was determined. This surface potential was measured using a wire loop probe contained in a shielded cylinder, and placed directly above the photoreceptor member surface. This loop was capacitively coupled to the photoreceptor surface so that the voltage of the wire loop corresponds to the surface potential. Also, the cylinder enclosing the wire loop was connected to the ground.

For this imaging member the acceptance potential was 800 volts, the residual potential was 100 volts, and the half decay exposure sensitivity was 40 ergs/cm$^2$. Further, the electrical properties of this photoreceptor member remained essentially uncharged for 1,000 cycles of repeated charging and discharging.

EXAMPLE IX

A layered photoresponsive imaging member comprised of Compound (II) in Merlon polycarbonate as the electron transport layer, and a trigonal selenium generator layer was fabricated as follows:

A 2 micron thick trigonal selenium photogenerator layer was fabricated on aluminized Mylar by repeating the procedure of Example VIII. A solution for the transport layer was then prepared by dissolving 5 grams of Compound (II), 2 grams of the diamine of Example VIII, and 13 grams of Merlon polycarbonate in 150 milliliters of methylene chloride, and 100 milliliters of 1,1,2-trichloroethane. Thereafter, the solution was spray coated on top of the photogenerator layer by means of a commercial spray gun in a spray booth at 20° C. and 35 percent relative humidity (R.H.). The resulting member was then dried in a forced air oven at 130° C. for 30 minutes resulting in a dry thickness for the transport layer of 10 microns. Subsequently, the imaging member was cooled to room temperature, followed by electrical testing in accordance with the procedure of Example VIII. Specifically, this imaging member was positively charged to fields of 60 volts/micron and discharged when exposed to white light of wavelengths of 400 to 700 nanometers. The half decay exposure sensitivity of this device was 40 ergs/cm$^2$.

EXAMPLE X

A layered photoresponsive imaging member comprised of Compound (III) in Vitel PE-100 polyester (Goodyear) as the electron transport layer, and trigonal selenium as the photogenerator was fabricated as follows:

A 2 micron trigonal selenium photogenerator layer was prepared on an aluminized Mylar substrate in accordance with the procedure was described in Example VIII. The solution for the transport layer was prepared by dissolving 0.35 gram of Compound (III), 0.13 gram of N,N'-diphenyl-N,N'-bis(3-methylphenyl)-1,1'-biphenyl-4,4'-diamine, and 0.31 gram of Vitel PE-100 polyester in 5 milliliters of methylene chloride. This solution was then coated by means of a Bird Film applicator over the photogenerator layer. Thereafter, the resulting member was dried in a forced air oven at 135° C. for 30 minutes, yielding a transport layer of a thickness of 12 microns. Electrical testing was carried out in accordance with the procedure of Example VIII. For this imaging member, the acceptance potential was 800 volts, and the half decay exposure sensitivity was 120 ergs/cm$^2$.

EXAMPLE XI

A layered photoresponsive device comprised of Compound (IX) as obtained in Example VII, as the transport layer, and amorphous selenium as the photogenerator, was fabricated as follows:

A 1 micron thick layer of amorphous selenium on a ball grained aluminum plate of a thickness of 7 mils was prepared by conventional vacuum deposition techniques. Vacuum deposition was accomplished at a vacuum of $10^{-6}$ torr, while the substrate was maintained at about 50° C. An electron transport layer on top of the amorphous selenium layer was obtained by coating a solution of 50 percent by weight each of Compound (IX) and poly(N-vinylcarbazole) in methylene chloride using a Bird Film applicator. This solution was prepared by dissolving 5 grams of Compound (IX), and 5 grams of poly(N-vinylcarbazole) in 70 grams of methylene chloride. Thereafter, the resulting device was dried in a forced air oven at 50° C. for 2 hours to form a 10 micron thick transport layer.

Electrical testing was affected by repeating the procedure of Example VIII, and substantially similar results were achieved.

EXAMPLE XII

A photoresponsive device comprised of Compound (IV) as the transporting molecule, and squarylium pigments as the photogenerator was prepared as follows:

A ball grained aluminum substrate was coated with a solution of 1 milliliter of 3-aminopropyltrimethoxysilane in 100 milliliters of ethanol. The coating was heated at 110° C. for 10 minutes, resulting in the formation of a 0.1 micron thick polysiloxane layer. A dispersion of a photogenerator prepared by ball milling a mixture of 0.075 gram of bis(N,N'-dimethylaminophenyl)squaraine and 0.13 gram of Vitel PE-200 polyester (Goodyear) in 12 milliliters of methylene chloride for 24 hours was then coated on top of the polysilane layer. After drying the coating in a forced air oven at 135° C. for 6 minutes, a 0.5 micron thick squarylium photogenerating layer was obtained.

A solution for the transport layer was then prepared by dissolving 1.0 gram of Compound (IV), prepared in accordance with Example IV, 0.3 gram of N-isopropylcarbazole, and 1.0 gram of Makrolon polycarbonate in 20 milliliters of methylene chloride. This solution was then coated over the above photogenerator layer using a Bird Film applicator. The resulting device was dried in a forced air oven at 135° C. for 30 minutes, resulting in a 20 micron thick electron transport layer.

Electrical testing was affected in accordance with the procedure of Example VIII. Specifically, the device was charged positively to fields of 50 volts/micron and discharged with 830 nanometers monochromatic light. For this imaging device, the half decay exposure sensitivity was 150 ergs/cm$^2$.

EXAMPLE XIII

A photoresponsive imaging device with a spray coated transport layer comprised of Compound (II), and a trigonal selenium photogenerator was fabricated as follows:

A 2 micron thick trigonal selenium photogenerator layer on an aluminized Mylar was prepared in accordance with the procedure of Example VIII. A solution for the transport layer was then prepared by dissolving 12 grams of Compound (II), 4 grams of N,N'-diphenyl-N,N'-bis(methylphenyl)-1,1'-biphenyl-4,4'-diamine, and 25 grams of Merlon polycarbonate in 200 milliliters of methylene chloride and 300 milliliters of 1,1,2-trichloroethane. This solution was spray coated over the photogenerator layer using a commercial spray gun in accordance with the procedure as described in Example IX. The coating was dried in a forced air oven at 135° C. for 30 minutes yielding a transport layer of a thickness of 6 microns.

Electrical testing was affected by repeating the procedure of Example VIII, and substantially similar results were achieved.

EXAMPLE XIV

A layered photoresponsive imaging member containing Compound (VIII) as synthesized in Example VI in a polycarbonate binder as the electron transport layer, and trigonal selenium as the photogenerator was prepared as follows:

A trigonal selenium photogenerator layer with a thickness of 2 microns was fabricated on an aluminized Mylar by repeating the procedure of Example VIII. A solution for the transport layer was prepared by dissolving 14 grams of Compound (VIII) and 26 grams of Merlon polycarbonate in 300 milliliters of methylene chloride and 200 milliliters of 1,1,2-trichloroethane. Thereafter, the solution was spray coated on top of the photogenerator layer by means of a commercial spray gun in a spray booth at 22° C. at 45 percent relative humidity. The resulting member was then dried in a forced air oven at 130° C. for 30 minutes, resulting in a dry thickness of the transport layer of 18 microns.

Electrical testing was carried out in accordance with the procedure of Example VIII. Specifically, this imaging member was positively charged to fields of 40 volts/micron and exposed to white light of wavelengths of 400 to 700 nanometers. The half decay exposure sensitivity of this device was 50 ergs/cm$^2$, and its electrical properties remained substantially the same after 1,000 cycles of repeated charging and discharging.

Other modifications of the present invention may occur to those skilled in the art based upon a reading of the present disclosure and these modifications are intended to be included within the scope of the present invention.

What is claimed is:

1. A process for the preparation of anthraquinodimethane derivatives and anthrone derivatives which comprises the condensation reaction of anthraquinones with active methylene compounds in the presence of an organic solvent, a Lewis acid, and a base.

2. A process in accordance with claim 1, wherein a substituted anthraquinone is selected.

3. A process in accordance with claim 1, wherein the active methylene compound is selected from the group consisting of malononitrile, and malonate.

4. A process in accordance with claim 1, wherein the Lewis acid is titanium tetrachloride.

5. A process in accordance with claim 1, wherein the base is pyridine.

6. A process in accordance with claim 1, wherein the reaction is affected at a temperature of from about 0° C. to about 30° C.

7. A process in accordance with claim 1, wherein there results the electron transporting compound 11,11,12,12-tetracyano-2-alkylanthraquinodimethane.

8. A process in accordance with claim 1, wherein there results the electron transporting compound 11,11,12,12-tetracyano-2-tert-butylanthraquinodimethane.

9. A process in accordance with claim 1, wherein there results the electron transporting compound 11,11,12,12-tetracyanoanthraquinodimethane.

10. A process in accordance with claim 1, wherein there results the electron transporting compound 11,11-dicyano-12,12-bis(ethoxycarbonyl)anthraquinodimethane.

11. A process accordance with claim 1, wherein there results the electron transporting compound 1-chloro-10-[bis(ethoxycarbonyl)methylene]anthrone.

12. A process in accordance with claim 1, wherein there results the electron transporting compound 1,8-dichloro-10-[bis(ethoxycarbonyl)methylene]anthrone.

13. A process in accordance with claim 1, wherein there results the electron transporting compound 1,8-dihydroxy-10-[bis(ethoxycarbonyl)methylene]anthrone.

14. A process in accordance with claim 1, wherein there results the electron transporting compound 1-cyano-10-[bis(ethoxycarbonyl)methylene)anthrone.

15. A process in accordance with claim 1, wherein the organic solvent is methylene chloride.

16. A process in accordance with claim 1, wherein there is selected for each mole of anthraquinone reactant from about 1 mole to 1.5 moles of active methylene compound, from about 2 to about 5 moles of Lewis acid, and from about 4 to about 20 moles of base.

17. A process in accordance with claim 1, wherein there is selected for each mole of anthraquinone 2 to 3 moles of active methylene compound, 3 to 5 moles of Lewis acid, and 6 to 25 moles of base.

18. A process in accordance with claim 1, wherein the reaction is accomplished at from about 0° C. to about 30° C.

19. A process for the preparation of anthraquinodimethane derivatives, which comprises reacting in the presence of an organic solvent anthraquinones, active methylene compounds, base and Lewis acid in accordance with the following reaction scheme:

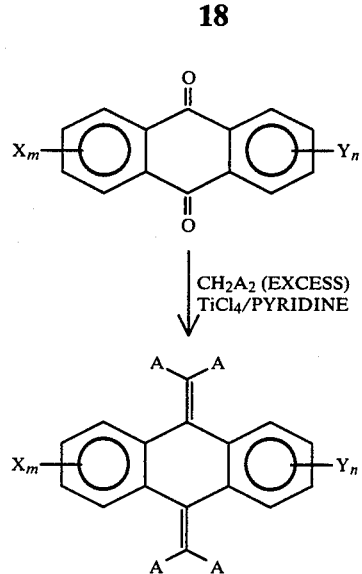

wherein A is selected from the group consisting of CN, and COOR, wherein R is an alkyl group or an aryl group; X and Y are independently selected from the group consisting of aryl, alkyl, halide, hydroxy, CN, $NO_2$, COR, and COOR; wherein R is an alkyl group; m is a number of from zero to 3; and n is a number of from zero to 3.

20. A process for the preparation of anthrone derivatives which comprises reacting in the presence of an organic solvent anthraquinone with active methylene compounds, a Lewis acid and a base in accordance with the following reaction scheme:

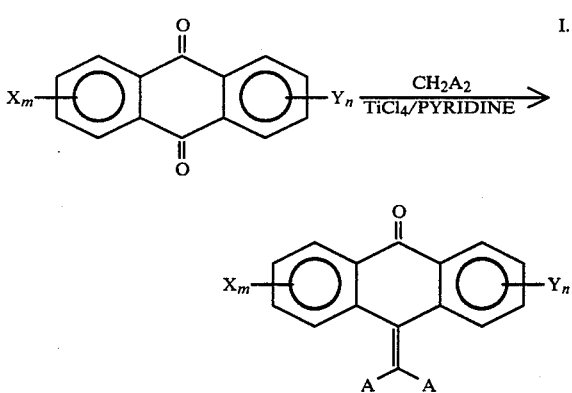

wherein A is independently selected from the group consisting of CN, and COOR, wherein R is an alkyl group or an aryl group; x and y are independently selected from the group consisting of aryl, alkyl, halide, hydroxy, CN, $NO_2$, COR, and COOR; wherein R is an alkyl group; m is a number of from zero to 3; and n is a number of from zero to 3.

21. A process in accordance with claim 19 or 20, wherein the reaction is accomplished at a temperature of from about 0° C. to about 30° C.

22. A process in accordance with claim 19 or 20, wherein the active methylene compound is selected from the group consisting of dinitromethane, malononitrile, malonate, and beta-diketone.

23. A process in accordance with claim 19, wherein from 1 mole of anthraquinone to from about 1 to about 1.5 moles of active methylene compound are selected, from about 2 to about 5 moles of Lewis acid, and from about 4 to about 20 moles of base are selected.

24. A process in accordance with claim 20, wherein from about 1 mole of anthraquinone to about 2 to about 3 moles of active methylene compound are selected, and from about 3 to about 5 moles of Lewis acid, and from about 6 to about 25 moles of base are selected.

25. A process in accordance with claim 19 or 20, wherein the reaction is affected in the presence of a chlorinated solvent.

26. A process in accordance with claim 25, wherein the chlorinated solvent is methylene chloride.

27. A process in accordance with claim 19 or 20, wherein the active methylene compound is malononitrile.

28. A process for the preparation of an anthraquinodimethane derivative comprising reacting in the presence of an organic solvent anthraquinone with an active methylene compound, a Lewis acid, and a base in accordance with the following reaction scheme:

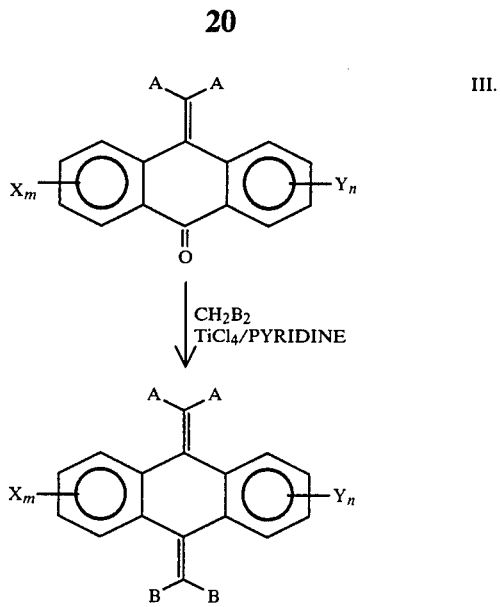

wherein the A substituents are COOR, the B substituents are CN; x and y are independently selected from the group consisting of aryl, alkyl, halide, hydroxy, CN, $NO_2$, COR, and COOR; m is a number of from zero to 3; and n is a number of from zero to 3.

29. A process for the preparation of anthraquinodimethane derivative and anthrone derivatives which consists essentially of the reaction of an anthraquinone with an active methylene compound selected from the group consisting of malononitrile, malonate, dinitromethane, and betadiketone in the presence of an organic solvent, a base, and a Lewis acid, which reaction is affected at a temperature of from about 0° C. to about 30° C.

30. A process in accordance with claim 29 wherein the organic solvent is methylene chloride.

31. A process in accordance with claim 29 wherein the Lewis acid is titanium tetrachloride.

32. A process in accordance with claim 29 wherein the base is pyridine.

33. A process in accordance with claim 29 wherein from 2 to 5 moles of Lewis acid, and 4 to 20 moles of base are selected.

* * * * *